United States Patent [19]

Schneider

[11] Patent Number: 4,457,713
[45] Date of Patent: Jul. 3, 1984

[54] DENTURE FORMING METHOD

[76] Inventor: Sidney Schneider, 576 Sussex Ave., Morristown, N.J. 07960

[21] Appl. No.: 427,020

[22] Filed: Sep. 29, 1982

[51] Int. Cl.³ .......................................... A61C 13/22
[52] U.S. Cl. ..................................... 433/171; 264/18
[58] Field of Search ............. 433/171, 167, 213, 214; 264/16, 17, 18

[56] References Cited

U.S. PATENT DOCUMENTS

| | | | |
|---|---|---|---|
| 3,064,354 | 11/1962 | Pos | 433/214 |
| 3,460,252 | 8/1969 | Schneider et al. | 433/171 |
| 3,464,111 | 9/1969 | Gillard | 433/171 |
| 3,621,575 | 11/1971 | Schneider et al. | 433/171 |
| 3,838,513 | 10/1974 | Katz et al. | 433/171 |
| 3,839,796 | 10/1974 | Hazar | 433/171 |
| 4,345,900 | 8/1982 | Katz et al. | 433/171 |
| 4,370,133 | 1/1983 | Stempel | 433/171 |

*Primary Examiner*—John J. Wilson
*Attorney, Agent, or Firm*—Michael J. Ram

[57] ABSTRACT

Disclosed is a method for forming a denture in-situ in the mouth of a dental patient. The method starts with a try-in of the teeth in wax formed to duplicate in shape the desired form of the finished denture. An in-situ impression of the try-in in alginate is followed by placing of the teeth in the resultant impressions in the alginate and subsequent acrylic buildup and in-situ forming and setting of the final acrylic denture.

9 Claims, 9 Drawing Figures

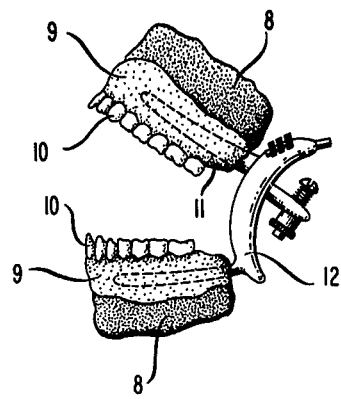
FIG. 1
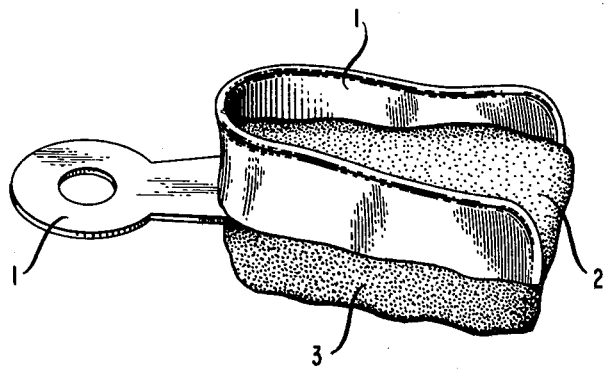
FIG. 2
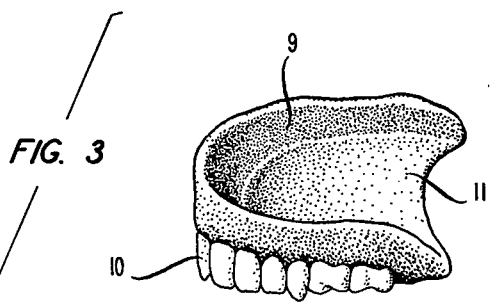
FIG. 3
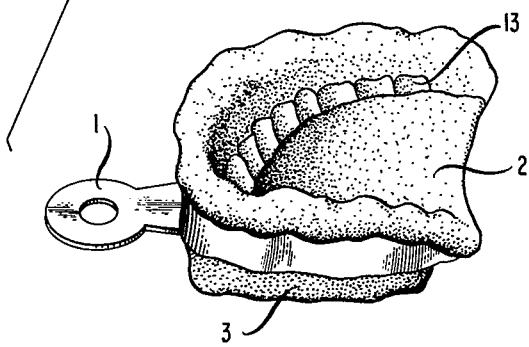

DENTURE FORMING METHOD

BACKGROUND OF THE INVENTION

The invention relates to the fabrication of artificial dentures and more particularly to the formation of the denture directly in the patient's mouth.

The procedure normally used to produce dentures starts with an impression of the edentulous gums from which a stone or plaster model is formed. Base plates are added to the models and they are mounted on an articulator. Teeth are mounted on the models using wax and the proper bite is established. The teeth in wax are then tried in the patient's mouth to confirm the fit and bite. Once confirmed the try-in is remounted on the model and a plaster cast of the wax model is made. Using well known procedures, dental base material is poured in the plaster mold and cured, forming a denture. All surfaces of the denture are then cleaned and polished.

This procedure may require the patient to make several visits to the dentist for molds to be made, the try-in to be tested and finished dentures to be fitted and adjusted. Because of the numerous steps required to produce a finished denture by this method and the possible inaccuracies in fit inherent in the process many dentures formed in this manner are not satisfactory.

Several patents heve addressed these problems by proposing devices and procedures for forming a denture directly in the patient's mouth. Key among these patents are U.S. Pat. Nos. 3,460,252, 3,621,575, 3,838,513 and 4,345,900. Each of these patents use a specially designed tray which is formable in some manner. U.S. Pat. No. 3,460,252 incorporates a silicone rubber to hold the teeth in the tray and a plastic film over the tray during forming of the denture to protect the tissue from possible harm by harsh chemicals used to form the denture. U.S. Pat. No. 3,621,575 utilizes a similiar tray and a shim conforming to the tray. U.S. Pat. No. 3,838,513 also uses a similar tray holding the teeth. The tray is filled with alginate with a spacer placed thereon and an impression of the edentulous gums are taken. Upon removal of the alginate impression from the mouth the alginate must be removed from the root portion of the teeth in the tray prior to adding the denture forming material. U.S. Pat. No. 4,345,900 is directed to a special formable tray readily shaped to the patient's mouth. This conformed tray is then used to form dentures using previously described methods such as in U.S. Pat. No. 3,621,575.

SUMMARY OF THE INVENTION

The above referenced Patents all start with the edentulous mouth with the objective of eliminating the need for the formation of the stone model. The present invention recognizes that there are some advantages in preparing the stone model and the subsequent try-in. The prior art devices may present some problems in properly fitting the formable tray to the broad range of patients and thus they require the dentist to stock an inventory of various sizes of trays and different shades of false teeth for placing therein. Also these trays may present problems in obtaining the proper bite. The try-in is a preliminary form of the denture skillfully shaped by the denturist to properly fit in the patients mouth and to present the best bite and occlusion. This can be confirmed by the dentist by placing the try-in in the patient's mouth and making any necessary adjustments prior to forming the finished denture. Utilizing the method of the present invention the denture is then immediately formed and finished, thus eliminating disadvantages of the standard method of denture formation. The denture is molded exactly to the shape of the patient's mouth at the time of the try-in thus eliminating variations introduced by the standard forming processes and eliminating the possibility that the patient's mouth dimensions may change while the denture is being produced.

The object of the present invention is to provide improvements in the formation of dentures, including particularly the in-situ formation of dentures.

Another object is to provide a new and improved method for the formation of dentures which have improved form and conformation over prior in-situ methods.

A still further object is to provide improved and more efficient procedures for in-situ formation of dentures starting from the try-in.

These and other objects of the present invention will be evident from the following description of the invention and accompanying drawings in which:

BRIEF DESCRIPTION OF THE DRAWINGS

FIG. 1 is a side view of the formed try-in applied to a stone model placed in an articulator.

FIG. 2 is a perspective view of the rim lock impression tray filled with alginate prior to taking an impression of the try-in.

FIG. 3 is an explode view of the impression tray and try-in showing the alginate with an impression of the try-in after removal from the mouth.

DESCRIPTION OF THE PREFERRED EMBODIMENTS

Figure 4:
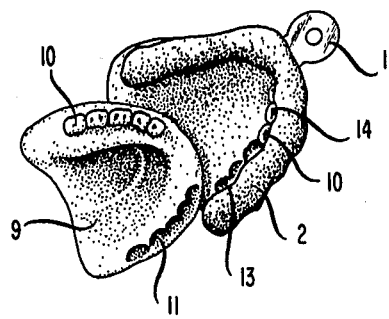
FIG. 4 is a perspective view of the impression tray with alginate having teeth placed therein.
Figure 4:
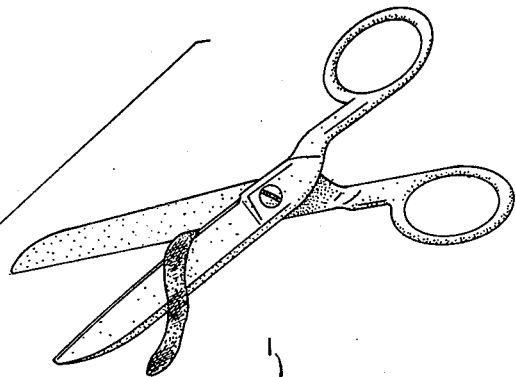

The following is representative of a step-by-step procedure for forming an upper denture in accordance with a preferred embodiment of the invention.

The material used in its construction are readily available to the dentist and denturist and are presently commonly used in dental procedures and the fabrication of dentures although they are not necessarily used in the manner described in the method of the present invention shown in FIGS. 1–9. The upper impression tray 1 is a device commonly used in the dental arts, in combination with alginate 2 or other suitable settable paste material for taking impressions of edentulous gums or normal teeth in the mouth for performing procedures such as the construction of stone models, the formation of caps or crowns, or as guides in orthodontic procedures, to name a few. The wax bite block 3 is also a material commonly used in the dental arts. The preferred material is biterim wax but other similarily functioning soft materials that retain a bite impression can be used.

Suitable cloth shim material 4, the components for preparing the hard acrylic mix 5, the semi-rigid acrylic mix 6 and the cloth coating liquid 7 are described in U.S. Pat. No. 3,621,575. While a broad range of shim materials can be used the preferred material is a porous fabric. Since the denture is fabricate from acrylic materials the best adhesion to the shim is obtained by using acrylic materials, in whole or in part, to fabricate the shim, for example DYNEL acrylic woven cloth.

In general, the rigid and semi-rigid acrylics 5 and 6 are cold curing pigmented mixtures consisting of a powder and a liquid. The powder is a polymer preferably of the acrylic family. Certain copolymers can also be used consisting of vinyl resins or styrene. The liquid material is preferably an acrylic monomer or mixture of acrylic monomers such as methyl methacrylate and butyl methacrylate. Such materials have been well known and used in the prior art, for example, as denture repair materials. The powder and liquid contain small quantities of known catalysts which interact to cause hardening of the mixture within a short time without any external heat source. The denture material may form a so-called "rigid" denture material or a more flexible type denture material. The distinction between rigid materials and other materials which are less rigid are well recognized in the denture art. Cold-curing resins used in the denture art often have varying tendency to cause discomfort during curing in contact with the gums of a dental patient primarily because of a stinging sensation which may or may not be reasonably tolerated by the patient. Contact of the curable resin with the gums of a patient's mouth can be avoided by enclosing the denture forming assembly in a thin envelope as described in U.S. Pat. No. 3,460,252. The use of such a protective envelope may be dispensed with however by selecting denture materials more suitable for direct contact with the gums without causing any substantial discomfort. Such a more suitable rigid type material is available commercially under the tradename "Duraliner." Components for the preferred semi-rigid denture material have been obtained on special order from the American Consolidated Mfg. Co. of Philadelphia, Pa., and is prepared by mixing 10.3 gms. of powder component obtained as special order component 3-A with 8.0 cc of a liquid component obtained as special order component 2-A. Other suitable rigid materials of similiar properties to "Duraliner" are available from Moyer, Inc. of Philadelphia, Pa.

The denture art well recognizes the distinction between hard or rigid denture materials and those other materials which are less rigid and softer. Such other materials are referred to herein as "semi-rigid" materials. A suitable distinction for purposes of the present invention and description thereof may be made according to the conventional 3-point Deflection Test given in the Interim Federal Specification W-R-00179a (DSA-DM) of Feb. 20, 1967, such that a "rigid" denture material will have a deflection not exceeding about 1.7 millimeters when determined in accordance with the standard test under an initial 1500 gm. load increasing to a maximum load of 2500 gm. while a "semi-rigid" denture material has a deflection exceeding 1.7 millimeters. Preferably the rigid material has a deflection between about 1.0 to 1.5 millimeters while the preferred semi-rigid material has a deflection between about 1.8 to 3.5 millimeters. The semi-rigid materials are preferred to be in combination with the rigid material in forming a denture in accordance with the invention.

The preferred cloth liquid 7 is the liquid monomer used in the semi-rigid acrylic mixture 6. However the liquid monomer used in the rigid (also referred to as hard) acrylic mixture or a different liquid acrylic monomer compatible with both of the acrylic mixtures can also be used. The semi-rigid monomer is preferred because it generally results in a lower exotherm during the in-situ denture formation and thus lesser discomfort to the patient from heat generation while the acrylic mixtures are setting.

To prepare the cold-curing rigid denture-forming material liquid monomer is added to the pigmented resin powder in a ratio of about 2 to 1 by weight and the mixture is vigorously mixed for about 15 seconds. The semi-rigid acrylic is prepared in a like manner by adding the liquid monomer to the semi-rigid pigmented powder followed by vigorous mixing.

An impression and wax bite of the patient's gums is taken once the swelling of the gums from any extractions has subsided. The impression of the gums is then transformed into a stone model 8 by standard denture techniques. A "try-in" 9, which consists of the teeth 10, later to be used in the denture, set in wax 11 is prepared. These teeth may be either porcelain or plastic, preferably acrylic. The teeth may have holes drilled in the root thereof or pins therein to aid in holding the tooth in the cured acrylic resin used to fabricate the denture. The try-in 9 is placed on the stone model 8 which is mounted in an articulator 12 and the desired bite is set (FIG. 1). The try-in 9 is next removed from the stone model 8, placed in the patient's mouth and the bite confirmed using a sheet of wax as a bite plate.

The normal procedure would now require the rearticulated try-in 9 to be returned to the dental lab where the lengthy process for converting the teeth-in-wax try-in into a finished denture proceeds.

The process of the invention starts at the point where the bite of the teeth-in-wax try-in 9 has been established in its desired form. The process which follows is for the formation of a finished upper denture 100 from the point where an upper try-in is properly positioned on the upper gums with the desired occlusion established. Similar procedures can be followed for preparing a lower denture or partial upper or lower dentures.

(A) An upper impression tray 1, preferably a rim lock impression tray, is prepared with a wax bite block 3 on the tray (FIG. 2). An adhesive for alginate, such as a spray-on tray adhesive available to the trade from Getz under the tradename HOLD can be added to the tray prior to addition of the alginate to aid in adhering said alginate to the tray.

(B) With the try-in still in place on the upper gums an impression is taken of said try-in 9 using the alginate 2 located in the tray 1. The wax 3 on the bottom surface of the tray 1 is used to register the bite of the lower set of teeth, dentures, or try-in as well as to maintain the proper position of the tray while the alginate is allowed to set (FIG. 3).

(C) Once the impression is established the tray 1 of alginate 2 with the try-in 9 therein is removed from the mouth and the try-in 9 is carefully removed from the alginate 2 leaving an impression 13 in the alginate 2 of the teeth 10 from the try-in 9 (FIG. 3). While it is preferred that the try-in be removed from the mouth still imbedded in the alginate, the tray and alginate can be removed first followed by the try-in.

(D) The teeth 10 of the try-in 9 are now removed from the wax 11. Any wax adhering thereto is removed from the teeth 10 and said teeth 10 are placed in their proper location in the impression 13 in the alginate 2 in the tray 1 (FIG. 4).

Figure 5:
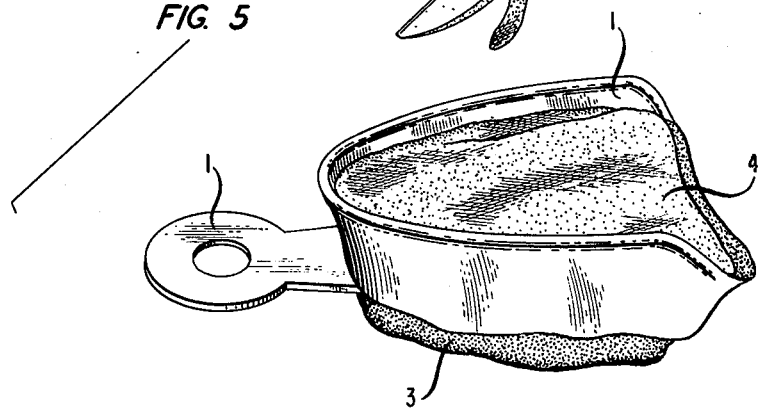
FIG. 5 is a perspective view of the tray of FIG. 4 with the cloth shim trimmed to fit therein.

(E) A piece of shim cloth 4 is trimmed to fit in the tray 1 over the alginate 2 and the exposed roots 14 of the teeth 10 (FIG. 5).

(F) After the shim 4 is properly sized it is thoroughly coated with the cloth coating liquid 7, and the wet shim cloth is draped over the stone model 8.

Figure 6:
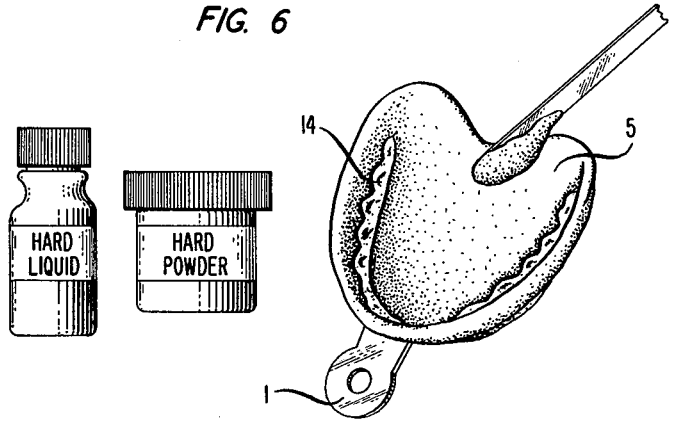
FIG. 6 is a perspective view of the tray of FIG. 4 after addition of the hard acrylic mixture.

(G) A portion of the two-part hard or rigid acrylic mixture is applied to the tooth roots 14 exposed above the alginate 2 so as to substantially cover the roots 14 (FIG. 6).

(H) The remainder of the hard or rigid acrylic mixture 5 is spread evenly on the wet shim cloth 4 which was draped on the stone model 8, the model with coated shim 4 is placed in the tray 1 over the alginate 2 and teeth 10 making sure the acrylic mixture 5 on the shim 4 is against the tooth roots 14 and then the model 8 is immediately removed leaving the shim 4 in the tray 1.

Figure 7:
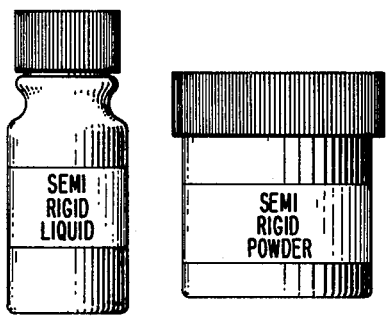
FIG. 7 is a perspective view of the tray, partly broken away, after addition of the wetted cloth shim and the soft acrylic mixture.
Figure 7:
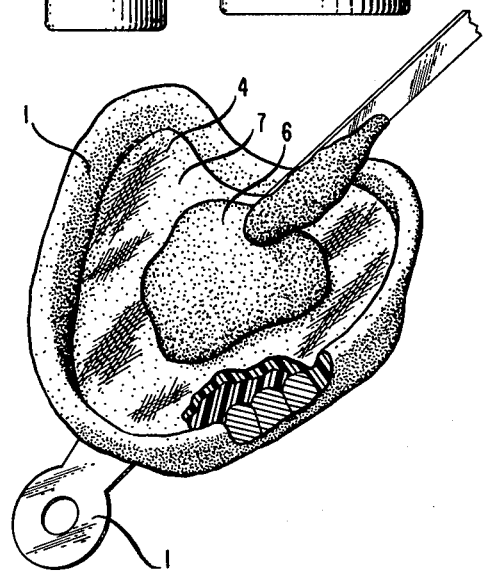

(I) Semi-rigid acrylic mixture 6 is applied evenly to the top of the wet shim cloth 4 (FIG. 7). The tray 1 now consists of a formed layer of alginate 2 with teeth 10 positioned therein, a layer of hard acrylic mixture thereon, a shim 4 wet with cloth treating liquid 7 on top of the hard acrylic mixture 5, and thereon a layer of semi-rigid acrylic mixture 6. Both the rigid or hard acrylic mixture 5 and the semi-rigid acrylic mixture 6 are still in a liquid state as they have not yet fully reacted and cured into a hardened material.

(J) Before the acrylic mixtures 5,6 have a chance to harden the tray 1 with its contents is placed in the patient's mouth and the preferred bite is established using the bite marks previously imbedded in the wax bite block 3.

(K) The tray 1 with its contents is retained in the mouth for approximately 6 minutes at which time the acrylic mixtures 5,6 will have sufficiently cured to hardened acrylic 15 and 16. The tray is then removed from the mouth and the formed denture 100 is removed from the alginate 2 in the tray. The denture 100, after simple trimming, finishing and polishing, all of which can be performed by the dentist in his office while the patient waits, is ready to wear.

Figure 8:
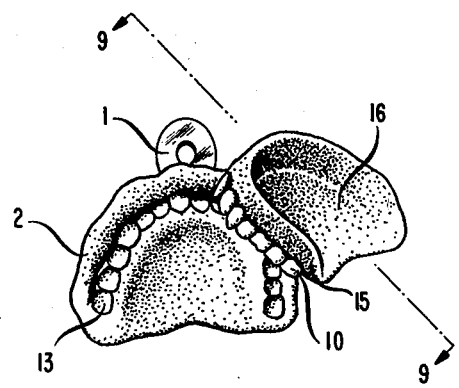
FIG. 8 is an exploded view taken from above of the formed denture as it is removed from the alginate mold.
Figure 9:
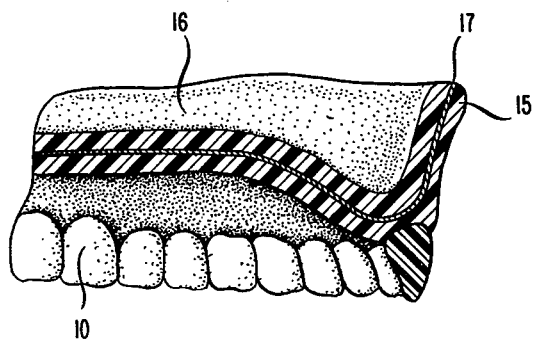
FIG. 9 is a section taken along line 9—9 of FIG. 8 showing the construction of the completed denture.

The complete denture 100 as shown in FIGS. 8 and 9, consists of teeth 10 imbedded in and secured to hardened rigid acrylic 15. Also partially imbedded in the hardened acrylic 15 is the shim cloth 4. On top of the shim cloth is the hardened semi-rigid acrylic 16. The cloth coating liquid 7 applied in the buildup procedure (Step F) above, reacted with both the hard (or rigid) and semi-rigid acrylic mixtures 5 and 6 placed on opposite sides of the shim 4 resulting in an acrylic 17 which now fills the interstices of the cloth 4, said acrylic 17 having the characteristics midway between those of the two acrylic layers.

While the above described procedure utilizes a hard or rigid mixture on the tooth side of the shim and a semi-rigid mixture on the patient palate side of the shim, the process of the invention contemplates the use of rigid acrylics on both sides of the shim or semi-rigid acrylics on both sides of the shim. However, it is preferred, to obtain the best adhesion between the teeth and the cured acrylic that at least the teeth roots are first coated with the rigid acrylic mixture. Also the addition of softer cushioning materials on the palate side of the denture are within the scope of the invention.

The procedure of the invention also contemplates the fabrication of a denture without the use of the shim cloth. This can be done in a one step procedure wherein enough of an acrylic mixture is added to the tray to form the desired end product. Also as an alternative, the rigid acrylic can be added as in the detailed procedure above. Rather then adding the shim a spacer approximating the thickness of the shim and semi-rigid acrylic is placed on the liquid rigid acrylic mixture and that assembly is placed in the patient's mouth for hardening. Upon hardening the assembly is removed from the mouth and the spacer is removed therefrom. The space which was taken up by the spacer is now filled with a second layer of liquid acrylic mixture, preferably a semi-rigid mixture and the assembly is once more position in the patient's mouth for the final hardening of the denture. While this procedure results in a product which does not have the reinforcing shim therein, eliminating the shim eliminates the possibility that the shim cloth may be exposed in the outer surface of the finished denture thus requiring additional finishing and polishing steps. Several different materials can be used as a spacer such as wax or a preformed plastic wafer.

It will be obvious to those skilled in the art that variations in the materials used or the procedure described herein can be resorted to without departing from the spirit of the invention.

What is claimed is:

1. A method for forming a denture in-situ in the mouth of a patient comprising:
   (A) providing a try-in of teeth set in a wax form, said try-in duplicating in shape the final desired denture,
   (B) placing said try-in on the edentulous gum in the patient's mouth,
   (C) with said try-in in place, forming an impression of same in alginate held in a tray,
   (D) removing said tray, alginate, and try-in from the mouth and placement of the teeth from said try-in in the tooth impressions formed in the alginate,
   (E) coating the exposed alginate impression and exposed roots of the teeth protruding above the alginate with curable liquid resins and forming said acrylic resin to the desired shape by implacing said tray with alginate, teeth and liquid acrylic resin in the patient's mouth until the acrylic has cured.

2. The method of claim 1 in which a hard acrylic resin and a semi-rigid acrylic resin are added sequentially to the alginate impression prior to implacing the tray back into the patient's mouth.

3. The method of claim 2 in which a cloth shim is placed on the curable hard acrylic prior to adding the semi-rigid acrylic.

4. The method of claim 3 in which the shim is coated with acrylic monomer prior to its placement on the hard acrylic.

5. The method of claim 1 in which
   (A) the acrylic resin is added to the tray,
   (B) a spacer is placed thereon and the tray is placed in the patient's mouth while the acrylic cures,
   (C) removing the tray from the patient's mouth and the spacer from over the acrylic in the tray,
   (D) adding a second acrylic layer to the tray, and
   (E) placing the tray in the patient's mouth for final forming and curing of the acrylic resin.

6. The method of claim 1 wherein the denture formed is an upper denture.

7. The method of claim 1 wherein the denture formed is a lower denture.

8. The method of claim 1 wherein the denture formed is a partial denture.

9. The method of claim 1 wherein a wax bite plate is added to the bottom of the tray prior to taking the impression of the try-in.

* * * * *